(12) United States Patent
Epinat et al.

(10) Patent No.: US 8,211,685 B2
(45) Date of Patent: Jul. 3, 2012

(54) I-*DMO*I DERIVATIVES WITH ENHANCED ACTIVITY AT 37° C AND USE THEREOF

(75) Inventors: Jean-Charles Epinat, Paris (FR); Emmanuel Lacroix, Paris (FR)

(73) Assignee: Cellectis, Romainville (FR)

( * ) Notice: Subject to any disclaimer, the term of this patent is extended or adjusted under 35 U.S.C. 154(b) by 690 days.

(21) Appl. No.: 11/587,987

(22) PCT Filed: Apr. 27, 2005
(Under 37 CFR 1.47)

(86) PCT No.: PCT/IB2005/001585
§ 371 (c)(1),
(2), (4) Date: Feb. 20, 2008

(87) PCT Pub. No.: WO2005/105989
PCT Pub. Date: Nov. 10, 2005

(65) Prior Publication Data
US 2008/0271166 A1 Oct. 30, 2008

(30) Foreign Application Priority Data
Apr. 30, 2004 (EP) .................................... 04291117

(51) Int. Cl.
| | |
|---|---|
| *C12N 9/14* | (2006.01) |
| *C12N 15/11* | (2006.01) |
| *C12N 15/00* | (2006.01) |
| *C12N 5/06* | (2006.01) |
| *A01H 5/00* | (2006.01) |
| *C12Q 1/68* | (2006.01) |

(52) U.S. Cl. ...................... 435/195; 435/320.1; 435/358; 435/6; 536/23.2

(58) Field of Classification Search .................. None
See application file for complete search history.

(56) References Cited

FOREIGN PATENT DOCUMENTS

| | | | |
|---|---|---|---|
| WO | WO02/099105 | * | 12/2002 |
| WO | 03/078619 | | 9/2003 |
| WO | 2004/031346 | | 4/2004 |

OTHER PUBLICATIONS

Chevalier et al: "Design, Activity, and Structure of a Highly Specific Artificial Endonuclease." Molecular Cell. Oct. 2002; vol. 10, pp. 895-905.*
Chevalier et al. (Molecular Cell. Oct. 2002; vol. 10, pp. 895-905).*
Epinat et al. (Nucleic Acids Research. Jun. 2003; 31(11): 2952-2962).*
Choulika—Sequence Alignment—2011.*
Silva, George H. et al., "Crystal Strucutre of the Thermostable Archaeal Intron-encoded Endonuclease I-DmoI", Journal of Molecular Biology, vol. 286, No. 4, pp. 1123-1136, 1999.
Lykke-Andersen, Jens et al., "Mapping metal ions at the catalytic centres of two intron-encoded endonudeases", The EMBO Journal, vol. 16, No. 11, pp. 3272-3281, 1997.

* cited by examiner

*Primary Examiner* — Scott Long
(74) *Attorney, Agent, or Firm* — Oblon, Spivak, McClelland, Maier & Neustadt, L.L.P.

(57) ABSTRACT

I-DmoI derivatives with enhanced cleavage activity at 37° C., said mutant comprising a sequence of a mutant of a I-DmoI endonuclease or a chimeric 5 derivative thereof including at least the first I-DmoIdomain, said sequence comprising the sub-situation of at least: (i) one of the residues in positions 4, 20, 49, 52, 92, 94 and/or 95 of said first I-DmoIdomain, and/or (ii) one of the residues in positions 101, 102, and/or 109 of the linker or the beginning of the second domain of I-DmoI, if present. 10 Polynucleotide encoding said derivatives, cell, animal or plant comprising said polynucleotide and use thereof for isolating meganucleases with new DNA target specificity.

22 Claims, 10 Drawing Sheets

Figure 2:
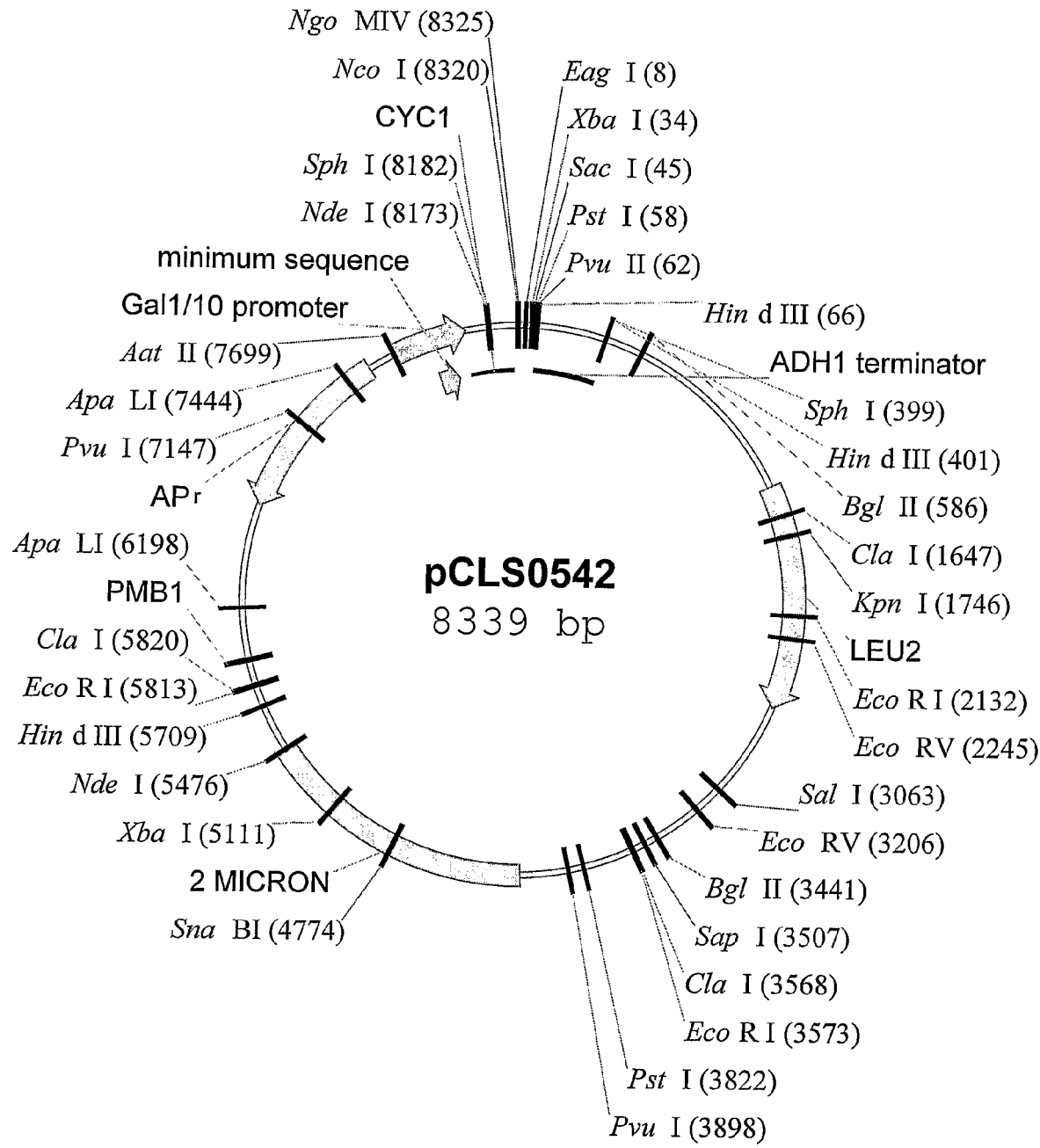

I-CreI:  5' TCAAAACGTCGTGAGACAGTTTGG 3'
         3' AGTTTTGCAGCACTCTGTCAAACC 5'

I-DmoI:  5' GCCTTGCCCGGGTAAGTTCCGGCGC 3'
         3' CGGAACGGGCCCATTCAAGGCCGCG 5'

C1D2:    5' TCAAAACGTCGTAAGTTCCGGCGC 3'
         3' AGTTTTGCAGCATTCAAGGCCGCG 5'

C2D2:    5' CCAAACTGTCTCAAGTTCCGGCGC 3'
         3' GGTTTGACAGAGTTCAAGGCCGCG 5'

Figure 1

```
                    1                                                50
I-DmoI-D1       MAHNNENVSGISAYLLGLIIGDGGLYKLKYKGNRSEYRVVITQKSENLIR
I-DmoI          MAHNNENVSGISAYLLGLIIGDGGLYKLKYKGNRSEYRVVITQKSENLIK
I-DmoI 1B24      MHNNENVSGISAYLLGLIIGDGGLYKLKYKGNRSEYRVVITQKSENLIK
I-DmoI P21505    MHNNENVSGISAYLLGLIIGDGGLYKLKYKGNRSEYRVVITQKSENLIK 51                                               100
I-DmoI-D1       QHFAPLMQFLIDELNVKSKIQIVKGDTRYELRVSSKKLYYYFANMQERIR
I-DmoI          QHIAPLMQFLIDELNVKSKIQIVKGDTRYELRVSSKKLYYYFANMLERIR
I-DmoI 1B24     QHIAPLMQFLIDELNVKSKIQIVKGDTRYELRVSSKKLYYYFANMLERIR
I-DmoI P21505   QHIAPLMQFLIDELNVKSKIQIVKGDTRYELRVSSKKLYYYFANMLERIR 101                                              150
I-DmoI-D1       LFNMREQIAFIKGLYVAEGDKTLKRLRIWNKNKALLEIVSRWLNNLGVRN
I-DmoI          LFNMREQIAFIKGLYVAEGDKTLKRLRIWNKNKALLEIVSRWLNNLGVRN
I-DmoI 1B24     LFNMREQIAFIKGLYVAEGDKTLKRLRIWNKNKALLEIVSRWLNNLGVRN
I-DmoI P21505   LFNMREQIAFIKGLYVAEGDKTLKRLRIWNKNKALLEIVSRWLNNLGVRN 151                                     195
I-DmoI-D1       TIHLDDHRHGVYVLNISLRDRIKFVHTILSSHLNPLPPEAAD---
I-DmoI          TIHLDDHRHGVYVLNISLRDRIKFVHTILSSHLNPLPPEAAD---
I-DmoI 1B24     TIHLDDHRHGVYVLNISLRDRIKFVHTILSSHLNPLPPE------
I-DmoI P21505   TIHLDDHRHGVYVLNISLRDRIKFVHTILSSHLNPLPPERAGGYT
```

Figure 6

```
                  1                                                50
DmoCre G20S      MVHNNENVSGISAYLLGLIISDGGLYKLKYKGNRSEYRVVITQKSENLIK
DmoCre v1        MAHNNENVSGISAYLLGLIIGDGGLYKLKYKGNRSEYRVVITQKSENLIK
DmoCre v4        MAHNNENVSGISAYLLGLIIGDGGLYKLKYKGNRSEYRVVITQKSENAIK
I-DmoI 1B24       MHNNENVSGISAYLLGLIIGDGGLYKLKYKGNRSEYRVVITQKSENLIK 51                                               100
DmoCre G20S      QHIAPLMQFLIDELNVKSKIQIVKGDTRYELRVSSKKLYYYFANMLERIR
DmoCre v1        QHIAPLMQFLIDELNVKSKIQIVKGDTRYELRVSSKKLYYYFANMLERIR
DmoCre v4        QAIAPDMQFLIDELNVKSKIQIVKGDTRYELRVSSKKLYYYFANMLERIR
I-DmoI 1B24      QHIAPLMQFLIDELNVKSKIQIVKGDTRYELRVSSKKLYYYFANMLERIR 101                                              150
DmoCre G20S      LFNMREQLAFLAGFVDGDGSIIAQIKPNQSYKFKHQLSLTFQVTQKTQRR
DmoCre v1        LFNMREQLAFLAGFVDGDGSIIAQIKPNQSYKFKHQLSLTFQVTQKTQRR
DmoCre v4        LFNMREQLAFLAGFVDGDGSIIAQIKPNQSYKFKHQLSLTFQVTQKTQRR
I-DmoI 1B24      LFNMREQIAFIKGLYVAEGDKTLKRLRIWNKNKALLEIVSRWLNNLGVRN 151                                              200
DmoCre G20S      WFLDKLVDEIGVGYVRDRGSVSDYILSEIKPLHNFLTQLQPFLKLKQKQA
DmoCre v1        WFLDKLVDEIGVGYVRDRGSVSDYILSEIKPLHNFLTQLQPFLKLKQKQA
DmoCre v4        WFLDKLVDEIGVGYVRDRGSVSDYILSEIKPLHNFLTQLQPFLKLKQKQA
I-DmoI 1B24      TIHLDDHRHGVYVLNISLRDRIKFVHTILSSHLNPLPPE 201                                              250
DmoCre G20S      NLVLKIIEQLPSAKESPDKFLEVCTWVDQIAALNDSKTRKTTSETVRAVL
DmoCre v1        NLVLKIIEQLPSAKESPDKFLEVCTWVDQIAALNDSKTRKTTSETVRAVL
DmoCre v4        NLVLKIIEQLPSAKESPDKFLEVCTWVDQIAALNDSKTRKTTSETVRAVL 251        264
DmoCre G20S      DSLSEKKKSSPAAD
DmoCre v1        DSLSEKKKSSPAAD
DmoCre v4        DSLSEKKKSSPAAD
```

Figure 9

SEQUENCE LISTING

<160> NUMBER OF SEQ ID NOS: 14

<210> SEQ ID NO 1

```
<211> LENGTH: 192
<212> TYPE: PRT
<213> ORGANISM: Desulfurococcus mobilis

<400> SEQUENCE: 1

Met Ala His Asn Asn Glu Asn Val Ser Gly Ile Ser Ala Tyr Leu Leu
 1               5                  10                  15

Gly Leu Ile Ile Gly Asp Gly Gly Leu Tyr Lys Leu Lys Tyr Lys Gly
                20                  25                  30

Asn Arg Ser Glu Tyr Arg Val Val Ile Thr Gln Lys Ser Glu Asn Leu
            35                  40                  45

Ile Arg Gln His Phe Ala Pro Leu Met Gln Phe Leu Ile Asp Glu Leu
 50                  55                  60

Asn Val Lys Ser Lys Ile Gln Ile Val Lys Gly Asp Thr Arg Tyr Glu
 65                  70                  75                  80

Leu Arg Val Ser Ser Lys Lys Leu Tyr Tyr Phe Ala Asn Met Gln
                85                  90                  95

Glu Arg Ile Arg Leu Phe Asn Met Arg Gln Ile Ala Phe Ile Lys
                100                 105                 110

Gly Leu Tyr Val Ala Glu Gly Asp Lys Thr Leu Lys Arg Leu Arg Ile
                115                 120                 125

Trp Asn Lys Asn Lys Ala Leu Leu Glu Ile Val Ser Arg Trp Leu Asn
    130                 135                 140

Asn Leu Gly Val Arg Asn Thr Ile His Leu Asp Asp His Arg His Gly
145                 150                 155                 160

Val Tyr Val Leu Asn Ile Ser Leu Arg Asp Arg Ile Lys Phe Val His
                165                 170                 175

Thr Ile Leu Ser Ser His Leu Asn Pro Leu Pro Pro Glu Ala Ala Asp
                180                 185                 190

<210> SEQ ID NO 2
<211> LENGTH: 188
<212> TYPE: PRT
<213> ORGANISM: Desulfurococcus mobilis

<400> SEQUENCE: 2

Met His Asn Asn Glu Asn Val Ser Gly Ile Ser Ala Tyr Leu Leu Gly
 1               5                  10                  15

Leu Ile Ile Gly Asp Gly Gly Leu Tyr Lys Leu Lys Tyr Lys Gly Asn
                20                  25                  30

Arg Ser Glu Tyr Arg Val Val Ile Thr Gln Lys Ser Glu Asn Leu Ile
            35                  40                  45

Lys Gln His Ile Ala Pro Leu Met Gln Phe Leu Ile Asp Glu Leu Asn
 50                  55                  60

Val Lys Ser Lys Ile Gln Ile Val Lys Gly Asp Thr Arg Tyr Glu Leu
 65                  70                  75                  80

Arg Val Ser Ser Lys Lys Leu Tyr Tyr Phe Ala Asn Met Leu Glu
                85                  90                  95

Arg Ile Arg Leu Phe Asn Met Arg Glu Gln Ile Ala Phe Ile Lys Gly
                100                 105                 110

Leu Tyr Val Ala Glu Gly Asp Lys Thr Leu Lys Arg Leu Arg Ile Trp
                115                 120                 125

Asn Lys Asn Lys Ala Leu Leu Glu Ile Val Ser Arg Trp Leu Asn Asn
    130                 135                 140

Leu Gly Val Arg Asn Thr Ile His Leu Asp Asp His Arg His Gly Val
145                 150                 155                 160
```

```
Tyr Val Leu Asn Ile Ser Leu Arg Asp Arg Ile Lys Phe Val His Thr
            165                 170                 175

Ile Leu Ser Ser His Leu Asn Pro Leu Pro Pro Glu
            180                 185
```

<210> SEQ ID NO 3
<211> LENGTH: 194
<212> TYPE: PRT
<213> ORGANISM: Desulfurococcus mobilis

<400> SEQUENCE: 3

```
Met His Asn Asn Glu Asn Val Ser Gly Ile Ser Ala Tyr Leu Leu Gly
  1               5                  10                  15

Leu Ile Ile Gly Asp Gly Gly Leu Tyr Lys Leu Lys Tyr Lys Gly Asn
             20                  25                  30

Arg Ser Glu Tyr Arg Val Val Ile Thr Gln Lys Ser Glu Asn Leu Ile
         35                  40                  45

Lys Gln His Ile Ala Pro Leu Met Gln Phe Leu Ile Asp Glu Leu Asn
     50                  55                  60

Val Lys Ser Lys Ile Gln Ile Val Lys Gly Asp Thr Arg Tyr Glu Leu
 65                  70                  75                  80

Arg Val Ser Ser Lys Lys Leu Tyr Tyr Tyr Phe Ala Asn Met Leu Glu
                 85                  90                  95

Arg Ile Arg Leu Phe Asn Met Arg Glu Gln Ile Ala Phe Ile Lys Gly
            100                 105                 110

Leu Tyr Val Ala Glu Gly Asp Lys Thr Leu Lys Arg Leu Arg Ile Trp
        115                 120                 125

Asn Lys Asn Lys Ala Leu Leu Glu Ile Val Ser Arg Trp Leu Asn Asn
    130                 135                 140

Leu Gly Val Arg Asn Thr Ile His Leu Asp Asp His Arg His Gly Val
145                 150                 155                 160

Tyr Val Leu Asn Ile Ser Leu Arg Asp Arg Ile Lys Phe Val His Thr
                165                 170                 175

Ile Leu Ser Ser His Leu Asn Pro Leu Pro Pro Glu Arg Ala Gly Gly
            180                 185                 190

Tyr Thr
```

<210> SEQ ID NO 4
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Ala His Asn Asn Glu Asn Val Ser Gly Ile Ser Ala Tyr Leu Leu
  1               5                  10                  15

Gly Leu Ile Ile Gly Asp Gly Gly Leu Tyr Lys Leu Lys Tyr Lys Gly
             20                  25                  30

Asn Arg Ser Glu Tyr Arg Val Val Ile Thr Gln Lys Ser Glu Asn Leu
         35                  40                  45

Ile Arg Gln His Phe Ala Pro Leu Met Gln Phe Leu Ile Asp Glu Leu
     50                  55                  60

Asn Val Lys Ser Lys Ile Gln Ile Val Lys Gly Asp Thr Arg Tyr Glu
 65                  70                  75                  80

Leu Arg Val Ser Ser Lys Lys Leu Tyr Tyr Tyr Phe Ala Asn Met Gln
                 85                  90                  95
```

```
Glu Arg Ile Arg Leu Phe Asn Met Arg Glu Gln Ile Ala Phe Ile Lys
            100                 105                 110

Gly Leu Tyr Val Ala Glu Gly Asp Lys Thr Leu Lys Arg Leu Arg Ile
            115                 120                 125

Trp Asn Lys Asn Lys Ala Leu Leu Glu Ile Val Ser Arg Trp Leu Asn
130                 135                 140

Asn Leu Gly Val Arg Asn Thr Ile His Leu Asp Asp His Arg His Gly
145                 150                 155                 160

Val Tyr Val Leu Asn Ile Ser Leu Arg Asp Arg Ile Lys Phe Val His
                165                 170                 175

Thr Ile Leu Ser Ser His Leu Asn Pro Leu Pro Pro Glu Ala Ala Asp
                180                 185                 190

<210> SEQ ID NO 5
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala His Asn Asn Glu Asn Val Ser Gly Ile Ser Ala Tyr Leu Leu
1               5                   10                  15

Gly Leu Ile Ile Gly Asp Gly Leu Tyr Lys Leu Lys Tyr Lys Gly
            20                  25                  30

Asn Arg Ser Glu Tyr Arg Val Val Ile Thr Gln Lys Ser Glu Asn Leu
            35                  40                  45

Ile Lys Gln His Ile Ala Pro Leu Met Gln Phe Leu Ile Asp Glu Leu
        50                  55                  60

Asn Val Lys Ser Lys Ile Gln Ile Val Lys Gly Asp Thr Arg Tyr Glu
65                  70                  75                  80

Leu Arg Val Ser Ser Lys Lys Leu Tyr Tyr Tyr Phe Ala Asn Met Leu
                85                  90                  95

Glu Arg Ile Arg Leu Phe Asn Met Arg Glu Gln Leu Ala Phe Leu Ala
            100                 105                 110

Gly Phe Val Asp Gly Asp Gly Ser Ile Ile Ala Gln Ile Lys Pro Asn
            115                 120                 125

Gln Ser Tyr Lys Phe Lys His Gln Leu Ser Leu Thr Phe Gln Val Thr
        130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
            180                 185                 190

Leu Lys Leu Lys Gln Lys Gln Ala Asn Leu Val Leu Lys Ile Ile Glu
        195                 200                 205

Gln Leu Pro Ser Ala Lys Glu Ser Pro Asp Lys Phe Leu Glu Val Cys
    210                 215                 220

Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
                245                 250                 255

Lys Lys Ser Ser Pro Ala Ala Asp
            260
```

<210> SEQ ID NO 6
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala His Asn Asn Glu Asn Val Ser Gly Ile Ser Ala Tyr Leu Leu
 1               5                  10                  15

Gly Leu Ile Ile Gly Asp Gly Gly Leu Tyr Lys Leu Lys Tyr Lys Gly
             20                  25                  30

Asn Arg Ser Glu Tyr Arg Val Val Ile Thr Gln Lys Ser Glu Asn Ala
         35                  40                  45

Ile Lys Gln Ala Ile Ala Pro Asp Met Gln Phe Leu Ile Asp Glu Leu
     50                  55                  60

Asn Val Lys Ser Lys Ile Gln Ile Val Lys Gly Asp Thr Arg Tyr Glu
 65                  70                  75                  80

Leu Arg Val Ser Ser Lys Lys Leu Tyr Tyr Tyr Phe Ala Asn Met Leu
                 85                  90                  95

Glu Arg Ile Arg Leu Phe Asn Met Arg Glu Gln Leu Ala Phe Leu Ala
            100                 105                 110

Gly Phe Val Asp Gly Asp Gly Ser Ile Ile Ala Gln Ile Lys Pro Asn
        115                 120                 125

Gln Ser Tyr Lys Phe Lys His Gln Leu Ser Leu Thr Phe Gln Val Thr
    130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
            180                 185                 190

Leu Lys Leu Lys Gln Lys Gln Ala Asn Leu Val Leu Lys Ile Ile Glu
        195                 200                 205

Gln Leu Pro Ser Ala Lys Glu Ser Pro Asp Lys Phe Leu Glu Val Cys
    210                 215                 220

Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
                245                 250                 255

Lys Lys Ser Ser Pro Ala Ala Asp
            260

<210> SEQ ID NO 7
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala His Asn Asn Glu Asn Val Ser Gly Ile Ser Ala Tyr Leu Leu
 1               5                  10                  15

Gly Leu Ile Ile Gly Asp Gly Gly Leu Tyr Lys Leu Lys Tyr Lys Gly
             20                  25                  30

```
Asn Arg Ser Glu Tyr Arg Val Val Ile Thr Gln Lys Ser Glu Asn Leu
            35                  40                  45
Ile Lys Gln His Ile Ala Pro Leu Met Gln Phe Leu Ile Asp Glu Leu
 50                      55                  60
Asn Val Lys Ser Lys Ile Gln Ile Val Lys Gly Asp Thr Arg Tyr Glu
 65                  70                  75                  80
Leu Arg Val Ser Lys Lys Leu Tyr Tyr Tyr Phe Ala Asn Met Leu
                85                  90                  95
Glu Arg Ile Arg Leu Phe Asn Met Arg Glu Gln Leu Ala Phe Leu Ala
                    100                 105                 110
Gly Phe Val Asp Gly Asp Gly Ser Ile Ile Ala Gln Ile Lys Pro Asn
                115                 120                 125
Gln Ser Tyr Lys Phe Lys His Gln Leu Ser Leu Thr Phe Gln Val Thr
    130                 135                 140
Gln Lys Thr Gln Arg Arg Trp Phe Leu Asp Lys Leu Val Asp Glu Ile
145                 150                 155                 160
Gly Val Gly Tyr Val Arg Asp Arg Gly Ser Val Ser Asp Tyr Ile Leu
                165                 170                 175
Ser Glu Ile Lys Pro Leu His Asn Phe Leu Thr Gln Leu Gln Pro Phe
                180                 185                 190
Leu Lys Leu Lys Gln Lys Gln Ala Asn Leu Val Leu Lys Ile Ile Glu
            195                 200                 205
Gln Leu Pro Ser Ala Lys Glu Ser Pro Asp Lys Phe Leu Glu Val Cys
    210                 215                 220
Thr Trp Val Asp Gln Ile Ala Ala Leu Asn Asp Ser Leu Thr Arg Lys
225                 230                 235                 240
Thr Thr Ser Glu Thr Val Arg Ala Val Leu Asp Ser Leu Ser Glu Lys
                245                 250                 255
Lys Lys Ser Ser Pro Ala Ala Asp
            260

<210> SEQ ID NO 8
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala His Asn Asn Glu Asn Val Ser Gly Ile Ser Ala Tyr Leu Leu
  1               5                  10                  15
Gly Leu Ile Ile Gly Asp Gly Gly Leu Tyr Lys Leu Lys Tyr Lys Gly
                 20                  25                  30
Asn Arg Ser Glu Tyr Arg Val Val Ile Thr Gln Lys Ser Glu Asn Ala
            35                  40                  45
Ile Lys Gln Ala Ile Ala Pro Asp Met Gln Phe Leu Ile Asp Glu Leu
 50                      55                  60
Asn Val Lys Ser Lys Ile Gln Ile Val Lys Gly Asp Thr Arg Tyr Glu
 65                  70                  75                  80
Leu Arg Val Ser Lys Lys Leu Tyr Tyr Tyr Phe Ala Asn Met Leu
                85                  90                  95
Glu Arg Ile Arg Leu Phe Asn Met Arg Glu Gln Leu Ala Phe Leu Ala
                    100                 105                 110
Gly Phe Val Asp Gly Asp Gly Ser Ile Ile Ala Gln Ile Lys Pro Asn
                115                 120                 125
```

```
Gln Ser Tyr Lys Phe Lys His Gln Leu Ser Leu Thr Phe Gln Val Thr
        130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
                180                 185                 190

Leu Lys Leu Lys Gln Lys Gln Ala Asn Leu Val Leu Lys Ile Ile Glu
            195                 200                 205

Gln Leu Pro Ser Ala Lys Glu Ser Pro Asp Lys Phe Leu Glu Val Cys
        210                 215                 220

Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
                245                 250                 255

Lys Lys Ser Ser Pro Ala Ala Asp
            260

<210> SEQ ID NO 9
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Val His Asn Asn Glu Asn Val Ser Gly Ile Ser Ala Tyr Leu Leu
1               5                   10                  15

Gly Leu Ile Ile Ser Asp Gly Leu Tyr Lys Leu Lys Tyr Lys Gly
            20                  25                  30

Asn Arg Ser Glu Tyr Arg Val Val Ile Thr Gln Lys Ser Glu Asn Leu
            35                  40                  45

Ile Lys Gln His Ile Ala Pro Leu Met Gln Phe Leu Ile Asp Glu Leu
        50                  55                  60

Asn Val Lys Ser Lys Ile Gln Ile Val Lys Gly Asp Thr Arg Tyr Glu
65              70                  75                  80

Leu Arg Val Ser Ser Lys Lys Leu Tyr Tyr Phe Ala Asn Met Leu
                85                  90                  95

Glu Arg Ile Arg Leu Phe Asn Met Arg Glu Gln Leu Ala Phe Leu Ala
            100                 105                 110

Gly Phe Val Asp Gly Asp Gly Ser Ile Ile Ala Gln Ile Lys Pro Asn
        115                 120                 125

Gln Ser Tyr Lys Phe Lys His Gln Leu Ser Leu Thr Phe Gln Val Thr
        130                 135                 140

Gln Lys Thr Gln Arg Arg Trp Phe Leu Asp Lys Leu Val Asp Glu Ile
145                 150                 155                 160

Gly Val Gly Tyr Val Arg Asp Arg Gly Ser Val Ser Asp Tyr Ile Leu
                165                 170                 175

Ser Glu Ile Lys Pro Leu His Asn Phe Leu Thr Gln Leu Gln Pro Phe
                180                 185                 190

Leu Lys Leu Lys Gln Lys Gln Ala Asn Leu Val Leu Lys Ile Ile Glu
            195                 200                 205

Gln Leu Pro Ser Ala Lys Glu Ser Pro Asp Lys Phe Leu Glu Val Cys
        210                 215                 220
```

```
Thr Trp Val Asp Gln Ile Ala Ala Leu Asn Asp Ser Lys Thr Arg Lys
225                 230                 235                 240

Thr Thr Ser Glu Thr Val Arg Ala Val Leu Asp Ser Leu Ser Glu Lys
            245                 250                 255

Lys Lys Ser Ser Pro Ala Ala Asp
            260

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcaaaacgtc gtgagacagt ttgg                                           24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gccttgccgg gtaagttccg gcgc                                           24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tcaaaacgtc gtaagttccg gcgc                                           24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccaaactgtc tcaagttccg gcgc                                           24

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Ala Gly Leu Ile Asp Ala Asp Gly
 1               5
```

I-*DMO*I DERIVATIVES WITH ENHANCED ACTIVITY AT 37° C AND USE THEREOF

CROSS-REFERENCE TO RELATED APPLICATIONS

The present application is a 35 U.S.C. §371 National Stage patent application of International patent application PCT/IB05/001585, filed on Apr. 27, 2005, which claims priority to European patent application EP 04291117.2, filed on Apr. 30, 2004.

The present invention relates to I-DmoI derivatives with enhanced cleavage activity at 37° C. compared to I-DmoI which is essentially active at high temperature (>50° C.) and displays little or no activity at 37° C. The invention also relates to a polynucleotide encoding said derivatives, to a cell, an animal or a plant comprising said polynucleotide and to their use for isolating meganucleases with new DNA target specificity.

Meganucleases are endonucleases, which recognize large (12-45 bp) DNA target sites. In the wild, meganucleases are essentially represented by homing endonucleases, a family of very rare-cutting endonucleases. It was first characterized by the use (in vivo) of the protein I-SceI (Omega nuclease), originally encoded by a mitochondrial group I intron of the yeast *Saccharomyces cerevisiae*. Homing endonucleases encoded by introns ORF, independent genes or intervening sequences (inteins) present striking structural and functional properties that distinguish them from "classical" restriction enzymes (generally from bacterial system R/MII). They have recognition sequences that span 12-40 bp of DNA, whereas "classical" restriction enzymes recognize much shorter stretches of DNA, in the 3-8 bp range (up to 12 bp for rare-cutter). Therefore, the homing endonucleases present a very low frequency of cleavage, even in the human genome.

Furthermore, general asymmetry of homing endonuclease target sequences contrasts with the characteristic dyad symmetry of most restriction enzyme recognition sites. Several homing endonucleases encoded by introns ORF or inteins have been shown to promote the homing of their respective genetic elements into allelic intronless or inteinless sites. By making a site-specific double-strand break in the intronless or inteinless alleles, these nucleases create recombinogenic ends, which engage in a gene conversion process that duplicates the coding sequence and leads to the insertion of an intron or an intervening sequence at the DNA level.

Homing endonucleases fall into 4 separated families on the basis of pretty well conserved amino acids motifs. For review, see Chevalier and Stoddard (Nucleic Acids Research, 2001, 29, 3757-3774). One of them is the dodecapeptide family (dodecamer, DOD, D1-D2, LAGLIDADG (SEQ ID NO: 14), P1-P2). This is the largest family of proteins clustered by their most general conserved sequence motif: one or two copies (vast majority) of a twelve-residue sequence: the dodecapeptide. Homing endonucleases with one dodecapeptide (D) are around 20 kDa in molecular mass and act as homodimers. Those with two copies (DD) range from 25 kDa (230 amino acids) to 50 kDa (HO, 545 amino acids) with 70 to 150 residues between each motif and act as monomer. Cleavage is inside the recognition site, leaving 4 nt staggered cut with 3'OH overhangs. I-CeuI, and I-CreI (166 amino acids) illustrate the homing endonucleases with one dodecapeptide motif (mono-dodecapeptide). I-DmoI (194 amino acids, SWISSPROT accession number P21505), I-SceI, PI-PfuI and PI-SceI illustrate homing endonucleases with two dodecapeptide motifs. Structural models using X-ray crystallography have been generated for I-CreI (PDB code 1g9y), I-DmoI (PDB code 1b24), PI-Sce I, PI-PfuI. Structures of I-CreI and PI-SceI (Moure et al., Nat Struct Biol, 2002, 9: 764-70) bound to their DNA site have also been elucidated leading to a number of predictions about specific protein-DNA contacts.

Despite an apparent lack of sequence conservation, structural comparisons indicate that LAGLIDADG (SEQ ID NO: 14) proteins, should they cut as dimers (like I-CreI) or single chain proteins (like I-DmoI), adopt a similar active conformation. In all structures, the LAGLIDADG (SEQ ID NO: 14) motifs are central and form two packed α-helices where a 2-fold (pseudo-) symmetry axis separates two monomers or apparent domains. For example, the LAGLIDADG (SEQ ID NO: 14) motif corresponds to residues 13 to 21 in I-CreI, and to positions 12 to 20 and 109 to 117, in I-DmoI. On either side of the LAGLIDADG (SEQ ID NO: 14) α-helices, a four β-sheet provides a DNA binding interface that drives the interaction of the protein with the half site of the target DNA sequence. I-DmoI is similar to I-CreI dimers, except that the first domain (residues 1 to 95) and the second domain (residues 105 to 194) are separated by a linker (residues 96 to 104) (Epinat et al., Nucleic Acids Res, 2003, 31: 2952-62).

Recently, hybrid homing endonucleases were also developed, by fusing two LAGLIDADG (SEQ ID NO: 14) nucleases I-DmoI and I-CreI. DmoCre (Epinat et al, precited and NCBI accession numbers CAE85311 and CAE85312) and E-DreI (Chevalier et al., Mol Cell, 2002, 10: 895-905) are two very similar proteins, consisting of the fusion of one of the two I-DmoI domains to I-CreI. For example, DmoCre consists of the residues 1 to 109 of I-DmoI fused to the residues 13 to 166 of I-CreI. The two hybrid or chimeric endonucleases differ only in the linker region, and are able to cleave novel, hybrid DNA targets, made of two moieties, one from the I-CreI cleavage site, the other from the I-DmoI cleavage site.

Endonucleases are requisite enzymes for today's advanced genetic engineering techniques, notably for cloning and analyzing genes. Homing endonucleases are very interesting as rare-cutter endonucleases because they have a very low recognition and cleavage frequency in large genome due to the size of their recognition site. Therefore, the homing endonucleases are used for molecular biology and for genetic engineering.

It has been shown that induction of double-stranded DNA cleavage at a specific site in chromosomal DNA induces a cellular repair mechanism, which leads to highly efficient recombination events at that locus (WO 96/14408; WO 00/46386; U.S. Pat. No. 5,830,729; Choulika et al., Mol Cell Biol, 1995. 15, 1968-73; Cohen-Tannoudji et al., Mol Cell Biol, 1998. 18, 1444-8; Donoho et al, Mol Cell Biol, 1998, 18, 4070-8; Rouet et al, Mol Cell Biol, 1994, 14, 8096-106).

Therefore, the introduction of the double-strand break is accompanied by the introduction of a targeting segment of DNA homologous to the region surrounding the cleavage site, which results in the efficient introduction of the targeting sequences into the locus (either to repair a genetic lesion or to alter the chromosomal DNA in some specific way). Alternatively, the induction of a double-strand break at a site of interest is employed to obtain correction of a genetic lesion via a gene conversion event in which the homologous chromosomal DNA sequences from another copy of the gene provide correct sequences to the (mutated) sequences where the double-strand break was induced. This latter strategy leads to the correction of genetic diseases either in which one copy of a defective gene causes the disease phenotype (such as occurs in the case of dominant mutations) or in which mutations occur in both alleles of the gene, but at different locations (as is the case of compound heterozygous mutations). Unfortunately, this method of genome engineering by induction of homologous recombination by a double-strand break is limited by the introduction of a recognition and cleavage site of a natural meganuclease at the position where the recombination event is desired. Despite the diversity of the homing endonuclease family, it is very unlikely to find a natural cleavage site in a sequence of interest. Thus, a lot of efforts have been devoted recently to develop meganucleases with novel specificities in living cells.

However, the identification of novel specificities in living cells requires that the meganuclease activity is detectable at mesophilic temperatures. Thus, such assays can be used to look for derivatives of endonucleases such as I-SceI which is active at 30-37° C., but not with thermophilic endonuclease, displaying no or residual activity at 37° C.

Therefore, to develop meganucleases with novel specificities in living cells, there is a need of new meganucleases which display significant activity at 37° C.

I-DmoI is encoded by an intron from the hyperthermophile archae *Desulfurococcus mobilis*, and has been shown to be essentially active at high temperature (>50° C.; Dalgaard et al., Proc Natl Acad Sci USA, 1993, 90: 5414-7), although some activity was also reported at lower temperature (Chevalier et al., Mol Cell, 2002, 10: 895-905). DmoCre is active essentially at high temperature (65° C.) with little or no activity at 37° C. (Epinat et al., precited).

The inventors have isolated mutants of I-DmoI and Dmo-Cre with an enhanced activity at 37° C., as determined by assays at 37° C. Such mutants carrying mutations in the first domain, the linker or the beginning of the second domain of I-DmoI can be used as initial scaffold for identifying new meganucleases with novel cleavage sites.

Therefore, the invention concerns a polypeptide comprising a sequence of a mutant of a I-DmoI homing endonuclease or a chimeric derivative thereof including at least the first I-DmoI domain, said sequence comprising the substitution of at least: (i) one of the residues in positions 4, 20, 49, 52, 92, 94, and/or 95 of said first I-DmoI domain, and/or (ii) one of the residues in positions 101, 102, and/or 109 of the linker or the beginning of the second domain of I-DmoI, if present.

According to the invention, the first I-DmoI domain corresponds to positions 1 to 95 in I-DmoI amino acid sequence, the I-DmoI linker to positions 96 to 104 and the beginning of the second I-DmoI domain to positions 105 to 109.

In the present invention, unless otherwise mentioned, the residue numbers refer to the amino acid numbering of the I-DmoI sequence SWISSPROT number P21505 or the structure PDB code 1b24.

The polypeptide mutants according to the present invention represent new I-DmoI derivatives which are active at 37° C. compared to I-DmoI which is essentially active at high temperature (>50° C.) and displays little or no activity at 37° C.

The invention encompasses the polypeptides comprising or consisting essentially of the sequence as defined above.

In particular, the invention encompasses:

a) mutants of—wild-type—I-DmoI (I-DmoI mutants) consisting of the first I-DmoI domain as defined above and the second I-DmoI domain (positions 105 to 194), separated by the I-DmoI linker, and b) mutants of hybrid or chimeric I-DmoI (hybrid or chimeric-Dmo mutants) consisting of the fusion of the first I-DmoI domain as defined above, to a sequence of a dimeric LAGLIDADG (SEQ ID NO: 14) homing endonuclease (I-CreI for example) or to a domain of another monomeric LAGLIDADG (SEQ ID NO: 14) homing endonuclease. In addition, the first I-DmoI domain and the sequence or the domain of the other homing endonuclease may be separated by a linker, for example the I-DmoI linker.

In addition to the monomeric mutants as defined in a) and b), the invention encompasses also heterodimeric mutants (heterodimeric-Dmo mutants) wherein one polypeptide is a mutant of the first I-DmoI domain as defined above, and the other polypeptide is a dimeric LAGLIDADG (SEQ ID NO: 14) homing endonuclease (I-CreI for example) or a domain of another monomeric LAGLIDADG (SEQ ID NO: 14) homing endonuclease.

The chimeric-Dmo or the heterodimeric-Dmo mutants may include the sequence or the domain of a LAGLIDADG (SEQ ID NO: 14) homing endonuclease selected from the group consisting of: I-Sce I, I-Chu I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-Mav I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; preferably, I-Sce I, I-Chu I, I-Dmo I, I-Csm I, PI-Sce I, PI-Pfu I, PI-Tli I, PI-Mtu I, and I-Ceu I; more preferably, I-Cre I, PI-Sce I, and PI-Pfu I; still more preferably I-Cre I.

The polypeptide of the invention may include genetic modifications (insertion, deletion, substitution, truncation) or chemical modifications in its sequence as defined above, which do not alter the cleavage activity of the resulting polypeptide at 37° C. The modifications may be situated within, or at one or both extremities of said polypeptide. Said modifications include with no limitation:

insertion of one or more residues at the NH$_2$ terminus and/or COOH terminus, for example: a methionine residue is introduced at the NH$_2$ terminus, a tag (epitope or polyhistidine sequence) is introduced at the NH$_2$ terminus and/or COOH terminus; said tag is useful for the detection and/or the purification of said polypeptide, and/or substitution of one or more residues, for example in positions 1, 47, 51, 55, and/or 107 (M1A, L47A, H51A, L55D, I107L) of the first domain, the linker or the beginning of the second domain of I-DmoI.

Figure 8:
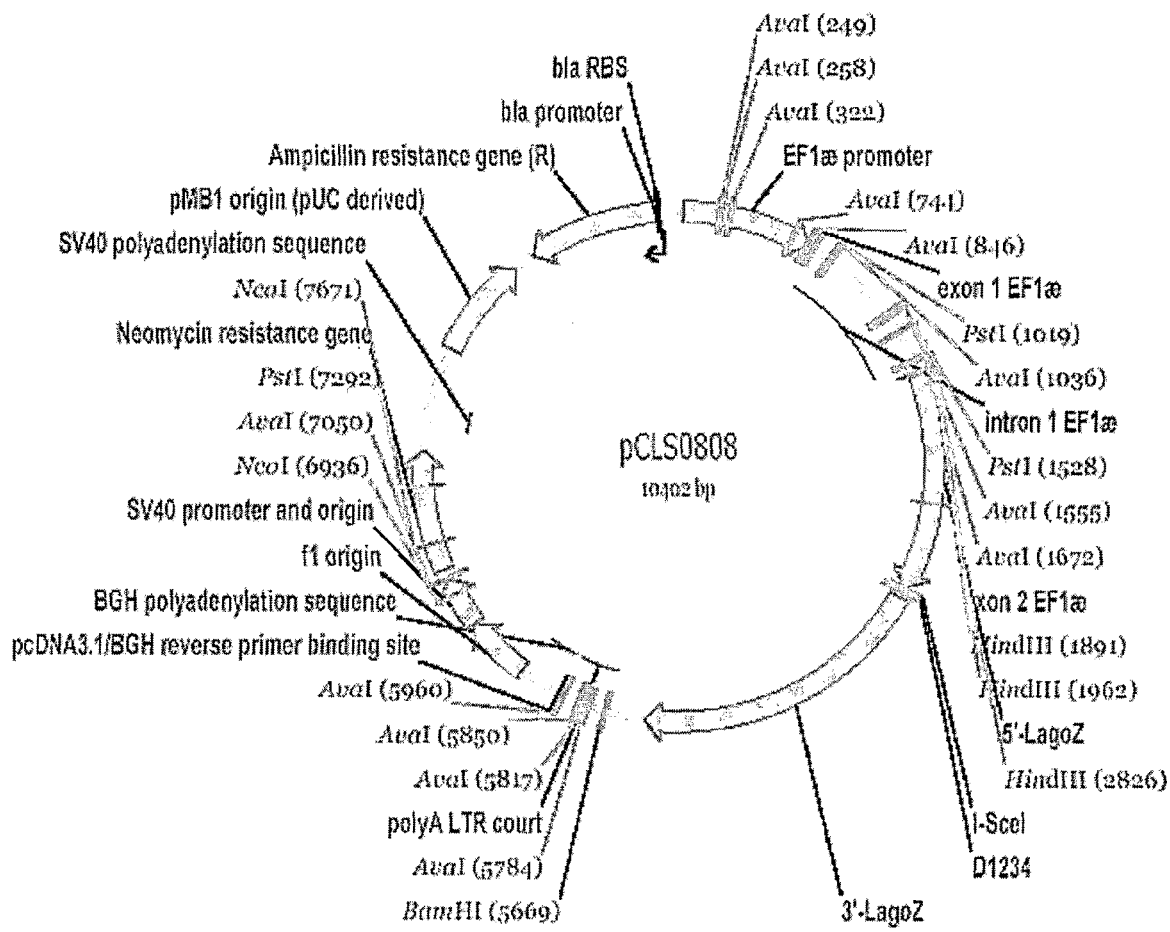

The cleavage activity of the I-DmoI derivative of the invention may be measured by a direct repeat recombination assay (FIG. 4), at 37° C., in yeast or mammalian cells, using a reporter vector. The reporter vector comprises two truncated, non-functional copies of a reporter gene (LacZ gene) and a cleavage site within the intervening sequence, cloned in a yeast (FIG. 3) or a mammalian expression vector (FIG. 8). The cleavage site (FIG. 1) is either a I-DmoI cleavage site (I-DmoI mutants) or a hybrid DNA target, made of two moieties, one from the cleavage site of the LAGLIDADG (SEQ ID NO: 14) homing endonuclease as defined above, the other from the I-DmoI cleavage site (hybrid I-DmoI mutants). Expression of a meganuclease which is active at 37° C. induces cleavage and recombination of the reporter vector, resulting in functional reporter gene expression that can be monitored by appropriate assay.

According to an advantageous embodiment of said polypeptide:

the asparagine in position 4 is changed to isoleucine (N4I),
the glycine in position 20 is changed to serine or alanine (G20S or G20A),
the lysine in position 49 is changed to arginine (K49R),
the isoleucine in position 52 is changed to phenylalanine (I52F),
the alanine in position 92 is changed to threonine (A92T),
the methionine in position 94 is changed to lysine (M94K),
the leucine in position 95 is changed to glutamine (L95Q),
the phenylalanine in position 101 (if present) is changed to cysteine (F101C), the asparagine in position 102 (if present) is changed to isoleucine (N102I), and/or the phenylalanine in position 109 (if present) is changed to isoleucine (F109I).

According to another advantageous embodiment of said polypeptide, it is a mutant of I-DmoI comprising the substitution of at least one of the residues in positions 49, 52, 92, 95 and/or 101.

Preferably, said I-DmoI mutant comprises at least: the substitution of the isoleucine in position 52, preferably to phenylalanine (I52F), and one or two additional substitutions of the residues in positions 49, 92, 95 and/or 101, as defined above. More preferably, it comprises the substitutions selected from the group consisting of: a) K49R, I52F and L95Q, b) I52F and L95Q, or c) I52F, A92T and F101C.

Preferably, said I-DmoI mutant derives from the sequence SEQ ID NO: 1, 2 or 3, most preferably from sequence SEQ ID NO: 1.

According to another advantageous embodiment of said polypeptide, it is a mutant of a chimeric-Dmo endonuclease consisting of the fusion of the first I-DmoI domain, to a sequence of a dimeric LAGLIDADG (SEQ ID NO: 14) homing endonuclease or to a domain of another monomeric LAGLIDADG (SEQ ID NO: 14) homing endonuclease, said mutant comprising the substitution of at least: (i) one of the residues in positions 4, 20, and/or 94, and/or (ii) one of the residues in positions 102 or 109, if present.

Preferably, the first I-DmoI domain is at the $NH_2$-terminus of the chimeric-Dmo endonuclease; consequently, the sequence or the domain of the other LAGLIDADG (SEQ ID NO: 14) homing endonuclease is at the COOH-terminus of said chimeric-Dmo endonuclease.

Preferably, said chimeric-Dmo mutant comprises a linker, preferably a I-DmoI linker consisting of at least 6 consecutive residues from the fragment 96 to 104 of I-DmoI.

Preferably, said chimeric-Dmo mutant derives from I-CreI (DmoCre), more preferably from a sequence selected from the group consisting of the sequences SEQ ID NO: 5 to 8.

Preferably, said chimeric-Dmo mutant comprises the substitutions selected from the group consisting of: a) G20S, b) G20A, c) M94K and N102I, or d) N4I and F109I.

According to another advantageous embodiment of said polypeptide it is a mutant of an heterodimeric-Dmo endonuclease wherein one polypeptide comprises the sequence of the first I-Dmo-I domain, said sequence comprising the substitution of at least one of the residues in positions 4, 20, 49, 52, 92, 94, and/or 95 as defined above, and the other polypeptide comprises a sequence of a dimeric LAGLIDADG (SEQ ID NO: 14) homing endonuclease or a domain of another monomeric LAGLIDADG (SEQ ID NO: 14) homing endonuclease.

Preferably, said dimeric LAGLIDADG (SEQ ID NO: 14) homing endonuclease is I-CreI.

The invention also concerns a polynucleotide encoding a polypeptide as defined above.

The invention also concerns a vector comprising said polynucleotide.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art.

Viral vectors include retrovirus, adenovirus, parvovirus (e.g. adenoassociated viruses), coronavirus, negative strand RNA viruses such as ortho-myxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomega-lovirus), and poxvirus (e.g., vaccinia, fowlpox and canarypox). Other viruses include Norwalk virus, togavirus, flavivirus, reoviruses, papovavirus, hepadnavirus, and hepatitis virus, for example.

Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP 1 for *S. cerevisiae*; tetracycline, rifampicin or ampicillin resistance in *E. coli.*

Preferably said vectors are expression vectors, wherein a sequence encoding a polypeptide of the invention is placed under control of appropriate transcriptional and translational control elements to permit production or synthesis of said protein. Therefore, said polynucleotide is comprised in an expression cassette. More particularly, the vector comprises a replication origin, a promoter operatively linked to said encoding polynucleotide, a ribosome site, an RNA-splicing site (when genomic DNA is used), a polyadenylation site and a transcription termination site. It also can comprise an enhancer. Selection of the promoter will depend upon the cell in which the polypeptide is expressed.

The invention also concerns a prokaryotic or eukaryotic host cell which is modified by a polynucleotide or a vector as defined above, preferably an expression vector.

The invention also concerns a non-human transgenic animal or a transgenic plant, characterized in that all or part of their cells are modified by a polynucleotide or a vector as defined above.

As used herein, a cell refers to a prokaryotic cell, such as a bacterial cell, or eukaryotic cell, such as an animal, plant or yeast cell.

The polynucleotide sequence encoding the polypeptide of the invention may be prepared by any method known by the man skilled in the art. For example, it is amplified from a cDNA template, by polymerase chain reaction with specific primers. Preferably the codons of said cDNA are chosen to favour the expression of said protein in the desired expression system.

The recombinant vectors comprising said polynucleotide may be obtained and introduced in a host cell by the well-known recombinant DNA and genetic engineering techniques.

The polypeptide of the invention may be obtained by culturing the host cell containing an expression vector comprising a polynucleotide sequence encoding said polypeptide, under conditions suitable for the expression of the polypeptide, and recovering the polypeptide from the host cell culture.

The invention also concerns the use of a polypeptide, a polynucleotide, a vector, a cell, an animal or a plant as defined above for the selection and/or the screening of meganucleases with novel DNA target specificity.

For example, the polynucleotide according to the invention may be mutagenized and the resulting mutants may be cloned in an appropriate expression vector and selected and/or screened for their ability to cleave a novel DNA target.

The cleavage activity of the resulting mutants may be measured by any appropriate mean. For example, it is measured by a direct repeat recombination assay, at 37° C., in yeast or mammalian cells, using a reporter vector. The reporter vector comprises two truncated, non-functional copies of a reporter gene (LacZ gene) and a novel cleavage site within the intervening sequence, cloned in a yeast or a mammalian expression plasmid. Expression of a meganuclease able to cleave the novel DNA target induces cleavage and recombination of the reporter plasmid, resulting in functional reporter gene expression that can be monitored by an appropriate assay.

The present invention will be further illustrated by the additional description and drawings which follows, which refers to examples illustrating the I-Dmo I derivatives according to the invention. It should be understood however that these examples are given only by way of illustration of the invention and do not constitute in anyway a limitation thereof.

Figure 3:
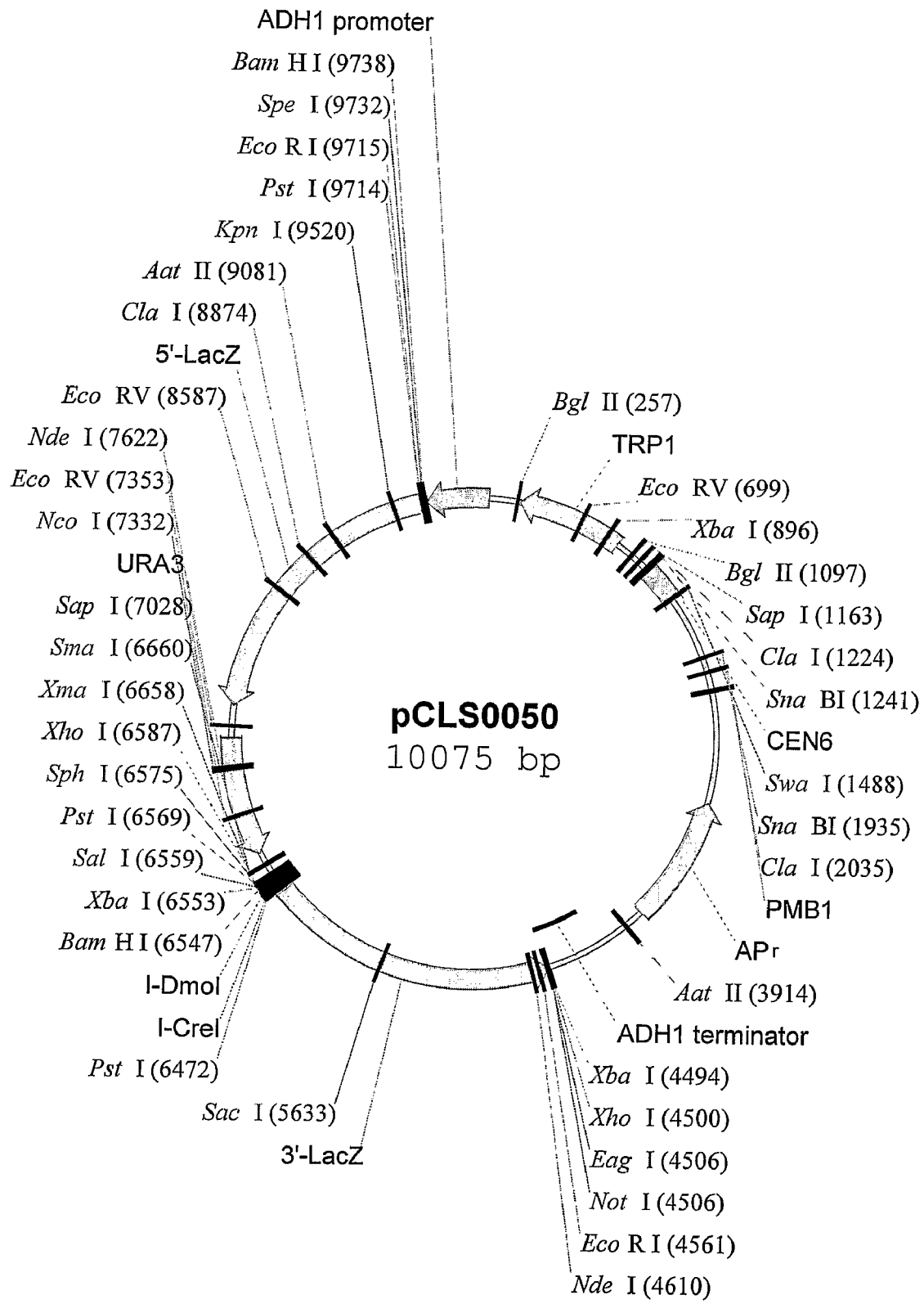
Figure 4:
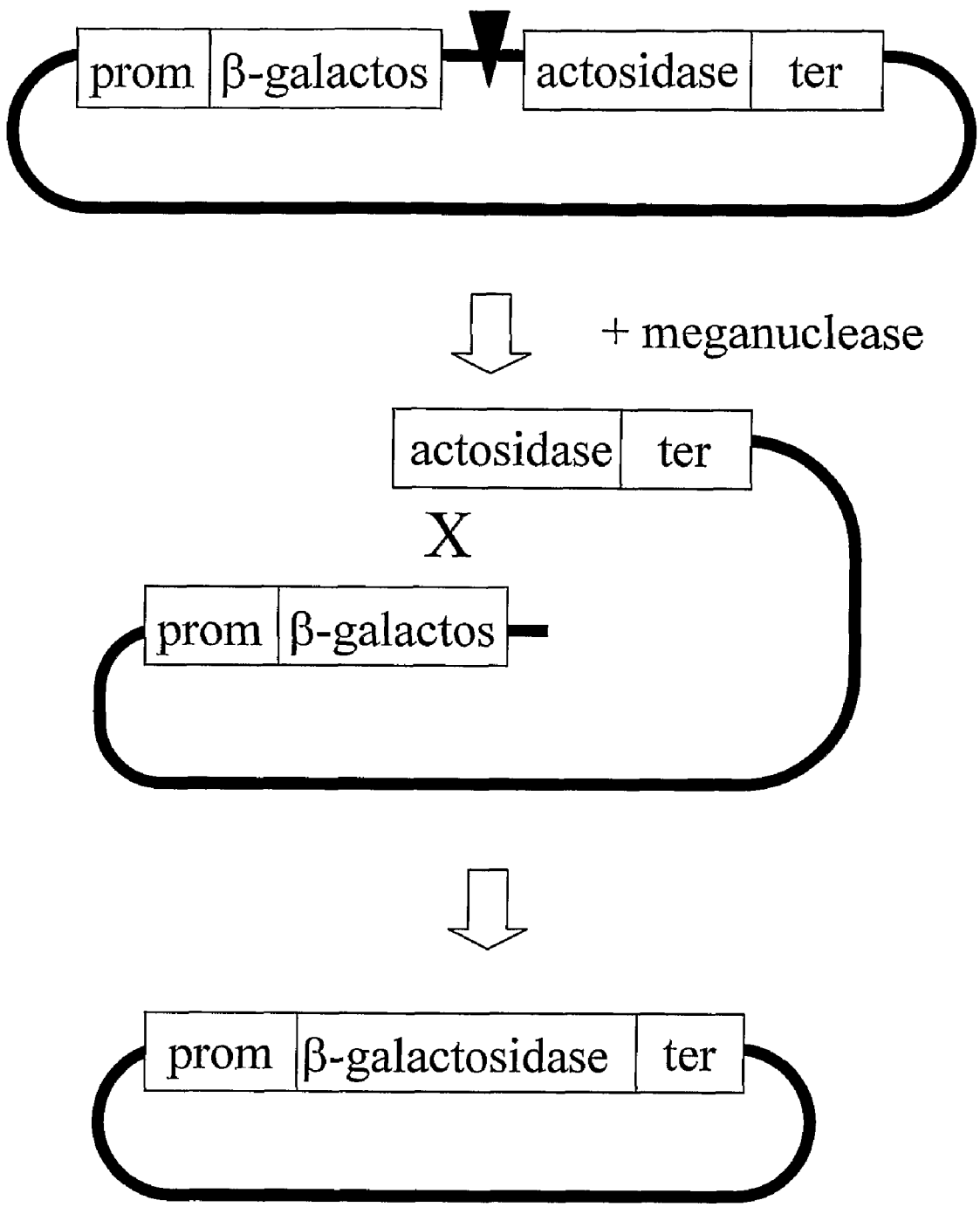
Figure 5:
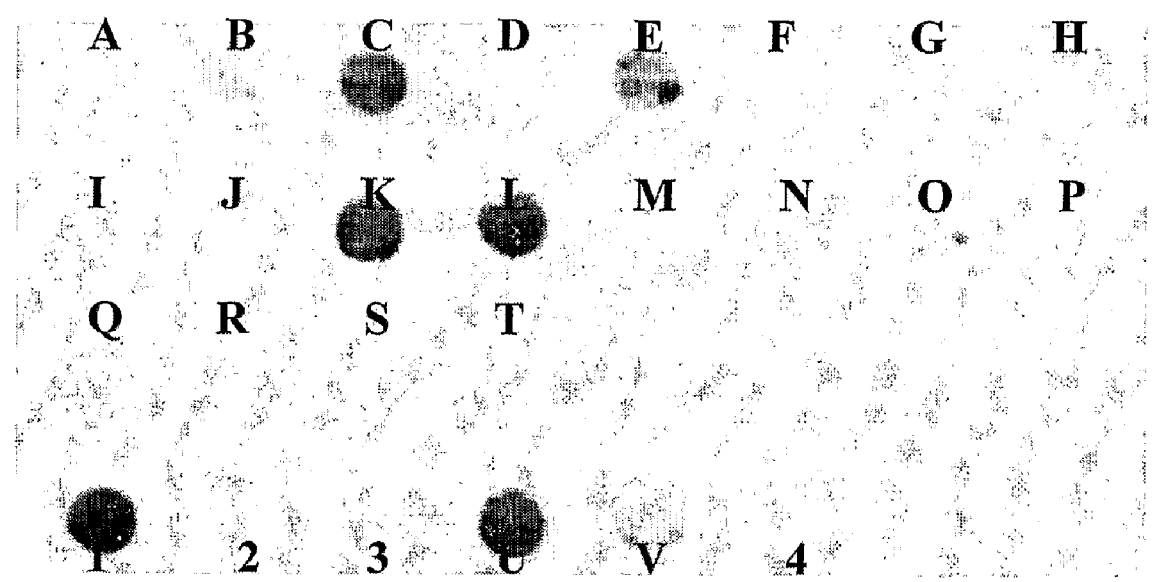

FIG. 1 represents I-CreI, I-DmoI, and hybrid C1D2 and C2D2 DNA target cut sites (SEQ ID NO:10-13), FIG. 2 represents the map of the yeast expression vector pCLS0542, used for the screening of the I-CreI and DmoCre mutants, FIG. 3 represents the map of the yeast reporter plasmid denominated pCLS0050; it contains CUT8, e.g. an I-CreI and an I-DmoI cleavage site as well as an URA3 selectable marker between two direct repeats internal the LacZ gene, FIG. 4 represents the principle of the recombination assay to detect meganuclease-induced recombination in yeast or mammal cells. Recombination occurs mostly by Single-Strand-Annealing (SSA). prom: promoter. ter: terminator, FIG. 5 represents the characterization of mutants obtained by random mutagenesis of I-DmoI sequence (SEQ ID NO: 1). I-DmoI and a set of I-DmoI mutants are tested against an I-DmoI target at 37° C. as described in example 1. DmoCre and pCL0S542 (empty vector) are also tested against an I-DmoI target whereas I-SceI is tested against a target with an I-SceI cleavage site. A-V: I-DmoI mutants A: K26N, Δ95; B: N4K, I52F, I60V; C: I52F, L95Q; D, I, J, M, P: wt (=I-DmoI); E: I19F, I52F, L55Q, F101C; F: Y13C, T76N; G, H, O: I52F; K, U: K49R, I52F, L95Q; L: non determined; N: M94L, L95Q; Q, R: I52F, F101C S, T: D7V, I52F; V: I52F, A92T, F101C; 1: I-SceI; 2: pCLS0542; 3: I-DmoI wild type, 4: DmoCre, FIG. 6 illustrates an example of I-DmoI mutant. The amino acid sequence of the D1 mutant (K49R, I52F, L95Q; SEQ ID NO: 4) is aligned with that of the initial I-DmoI sequence (SEQ ID NO: 1) used to generate the mutants. I-DmoI 1B24 (SEQ ID NO:2): sequence corresponding to the structure code 1b24 in the PDB protein structure data base. I-DmoI P21505 (SEQ ID NO:3): sequence corresponding to the number P21505 in the SWISSPROT sequence data base. Residue number for I-DmoI mutants refers to the amino acid numbering of the sequence SWISSPROT P21505 or the structure code PDB 1b24. For example, K49R mutation corresponds to the mutation of the residue in position 50 of SEQ ID NO:4.

Figure 7:
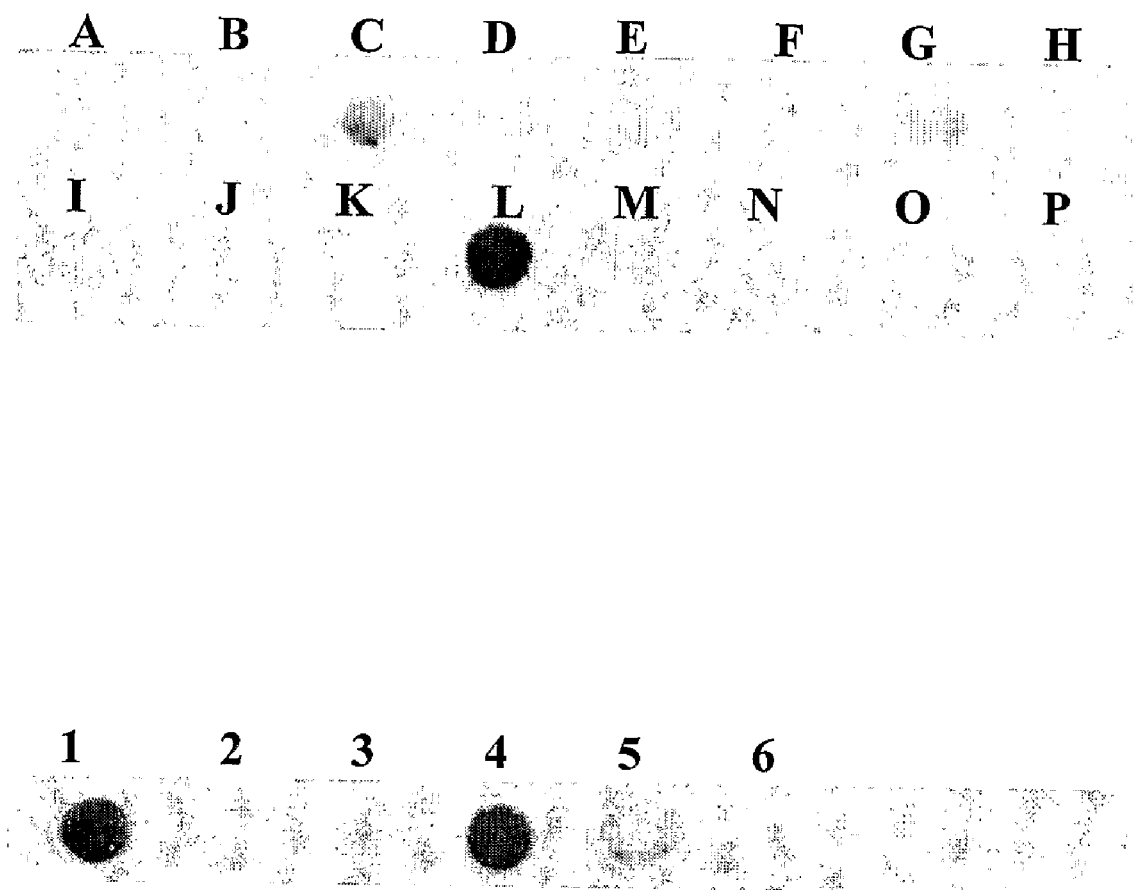

FIG. 7 represents the characterization of mutants obtained by directed mutagenesis I-DmoI and a set I-DmoI mutants obtained by directed mutagenesis are tested against an I-DmoI target at 37° C. as described in example 1. DmoCre and pCLS0542 (empty vector) are also tested against an I-DmoI target whereas I-SceI is tested against a target with an I-SceI cleavage site. A-V: I-DmoI mutants; A: G20S; B: K49R; C: I52F; D: A92T; E: L95Q; F: F101C; G: K49R/I52F; H: K49R/A92T; I: K49R/L95Q; J: K49R/F101C; K: I52F/A92T; L: I52F/L95Q; M: I52F/F101C; N: A92T/L95Q; O: A92T/F101C; P: L95Q/F101C; 1: I-SceI; 2: pCLS0542; 3: I-DmoI wild type; 4: 4: K49R, I52F, L95Q; 5: I52F, A92T, F101C; 6: DmoCre, FIG. 8 represents the structure of a reporter plasmid for mammalian cell assay. The pCLS0808 plasmid contains I-DmoI cleavage site between two small direct repeats within the LacZ gene.

FIG. 9 illustrates an example of DmoCre mutant. The amino acid sequence of the DC G20S mutant (A1 V, G20S; SEQ ID NO: 9) is aligned with that of the initial DmoCre sequence (DmoCre v1 ; SEQ ID NO: 5) used for the generation of the mutants. DmoCre v4 (SEQ ID NO: 6): sequence corresponding to the DmoCre construct described in Epinat et al., precited. Residue number for DmoCre mutants refer to the amino acid numbering of the sequence SWISSPROT P21505 or the structure PDB 1b24 (SEQ ID NO: 2). For example, A1V mutation corresponds to the mutation of the residue in position 2 of SEQ ID NO: 9.

Figure 10:
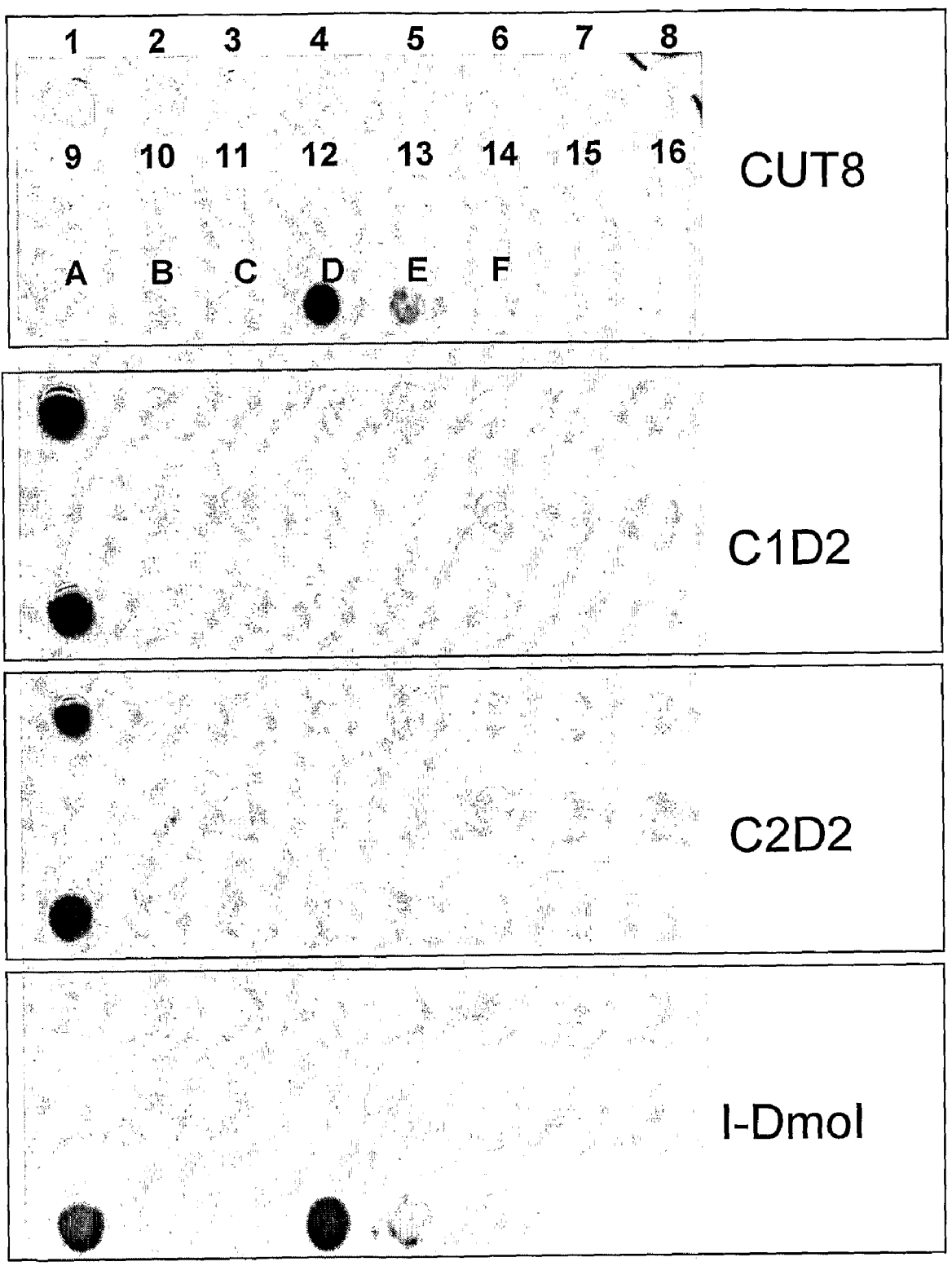

FIG. 10 represents the cleavage profile of a set of mutants in yeast. Here, the CUT8 (I-DmoI+I-CreI cleavage sites), I-DmoI, C1D2 and C2D2 cleavage sites are assayed. In each panel, I-SceI is also assayed with an I-SceI cleavage site, for positive control. All the other proteins are assayed with the target indicated on the right of the panel. A: I-SceI; B: empty expression vector; C: I-DmoI; D: K49R, I52F, L95Q I-DmoI mutant (see example 1); E: I52F, A92T, F101C I-DmoI mutant (see example 1); F: DmoCre. 1: G20S; 2: K49R; 3: I52F; 4: A92T; 5: L95Q; 6: F101C; 7: K49R/I52F; 8: K49R/A92T; 9: K49R/L95Q; 10: K49R/F101C; 11: I52F/A92T; 12: I52F/L95Q; 13: I52F/F101C; 14: A92T/L95Q; 15: A92T/F101C; 16: L95Q/F101C.

EXAMPLE 1

Characterization of I-DmoI Mutants with an Enhanced Activity at 37° C.

DNA manipulations were performed using classical methods, according to standard procedures as those described in *Current Protocols in Molecular Biology* (Frederick M. AUSUBEL, 2000, Wiley and son Inc, Library of Congress, USA).

1) Material and Methods

Plasmids

A set of I-DmoI mutants expression plasmids were constructed by random or directed mutagenesis of the I-DmoI coding sequence (SEQ ID NO: 1) and subcloning of the resulting sequences into the yeast expression plasmid pCLS0542 (galactose inducible promoter, LEU2 selectable marker and 2 micron origin of replication, FIG. 2).

A reporter plasmid was constructed according to the strategy described in Epinat et al., precited; pCLS0050 comprises a modified LacZ gene with two direct repeats of 825 base pairs separated by 1.3 kb containing a URA3 selectable marker and a I-DmoI cleavage site (FIG. 3).

Yeast Assay

Yeast of a (FYBL2/7B: a, ura3Δ851, trpIΔ63, leu2ΔI, lys2Δ202) and alpha (FYC2/6A: alpha, trpIΔ63, leu2ΔI, his3Δ200) mating type, transformed respectively with the reporter plasmid and the I-DmoI mutant expression plasmid, were grown overnight in selective medium. Then, 2 μl of a and alpha yeast culture were mixed in a final volume of 25 μl of YPD medium (rich media, glucose source) and incubated over night at 30° C. without shaking. 2 μl of the suspension was laid on selective medium, for selection of the diploids, with galactose as a carbon source, for induction of strong meganuclease expression. Plates were incubated 24 hours at 30° C. and 48 hours at 37° C., before X-Gal staining. For staining, a classic qualitative X-Gal Agarose Overlay Assay was used. Each plate was covered with 2.5 ml of 1% agarose in 0.1 M Sodium Phosphate buffer, pH 7.0, 0.2% SDS, 12% Dimethyl Formamide (DMF), 14 mM β-mercaptoethanol, 0.4% X-Gal, at 60°. Plates were incubated at 37° C.

2) Results

I-DmoI mutants with a putative enhanced cleavage activity were generated and assayed in yeast for their ability to induce the specific recombination of a reporter plasmid containing a SSA (Single Strand Annealing) β-galactosidase target.

In diploids, expression of an active meganuclease induces cleavage and recombination of the reporter plasmid resulting in a functional LacZ gene that can be monitored by X-Gal staining (FIG. 4).

Profile of the different clones is shown in FIG. 5. Fifteen clones (B, C, E, G, H, K, L, N, O, Q-V) display a blue coloration, ranging from light (Q-T) to dark (C, K, L) blue. Sequencing of the plasmid transformed into these yeast clones showed that the positives present at least nine different sequences (one sequence could not be recovered), each containing the substitution of one or more residues in positions 49, 52, 92, 95 and/or 101. Results are summarized in Table I. An example of mutant I-DmoI protein corresponding to the sequence SEQ ID NO: 4, is shown in FIG. 6.

TABLE I

I-DmoI mutant and cleavage activity in yeast cells at 37° C.

| Mutant* | Activity at 37° C. yeast cells |
|---|---|
| I-DmoI | − |
| K49R, I52F, L95Q | + |
| I52F, A92T, F101C | + |
| I52F | + |
| I52F, F101C | + |
| D7V, I52F | + |
| I52F, L95Q | + |
| N4K, I52F, I60V | + |
| I19F, I52F, L55Q, F101C | + |
| M94L, L95Q | + |
| Y13C, T76N | − |
| K26N, Δ95 | − |
| G20S | − |
| K49R/L95Q | + |
| K49R | + |
| K49R/F101C | + |
| A92T | + |
| I52F/L95Q | + |
| L95Q | + |
| I52F/F101C | + |
| F101C | + |
| A92T/L95Q | + |
| K49R/I52F | + |
| A92T/F101C | + |
| K49R/A92T | + |
| L95Q/F101C | + |
| I52F | + |
| I52F/A92T | + |

*Numeration of the amino acids is according to PDB code Ib24 or SWISSPROT P21505. K49R mutation means amino acid 49 is K in I-DmoI wild-type and R in the mutant.

Since mutants displayed often several mutations (example: K49R, I52F, L95Q), in order to assess the impact of each individual substitution, single mutants were generated. A G20S mutant was also generated. This mutant confers an enhanced activity to the DmoCre protein at 37° C. (see example 2), and since I-DmoI and DmoCre share the same NH2-terminal aminoacids (see example 2), this mutation could be expected to result in a similar effect with I-DmoI.

Characterization of these mutants is shown in FIG. 7 and results are summarized in Table I. Several mutants containing the substitution of at least one of the residues in position 52, 95, 49, 92 and/or 101, were shown to have indeed an enhanced activity in yeast at 37° C. Interestingly, the G20S mutation has no effect on I-DmoI activity at 37° C. The activity of the mutants was also detected at 37° C. in an in vitro cleavage assay according to the procedure described in Epinat et al., precited.

EXAMPLE 2

Characterization of Chimeric-Dmo (DmoCre) Mutants with an Enhanced Activity at 37° C.

1) Material and Methods

Plasmids

The mutant I-DmoI coding sequences were transferred in a vector designed for expression in mammalian cells (pTriex4-hygro, NOVAGENE). A mammalian version of the reporter plasmid was constructed using a strategy similar to that described in Epinat et al., precited (FIG. 8); the promoter and the termination sequences of the yeast plasmid were replaced by an EF1α promoter and a BGH polyadenylation sequence.

Mammalian Cells Assays

CHO cells were co-transfected by the reporter plasmid and the I-DmoI mutant expression plasmid with Superfect transfection reagent, according to the supplier (Qiagen) protocol. 72 hours after transfection, cells were rinsed twice with PBS1X and incubated in lysis buffer (Tris-HCl 10 mM pH7.5, NaCl 150 mM, Triton X100, 0.1%, BSA, 0.1 mg/ml, protease inhibitors). Lysate was centrifuged and the supernatant used for protein concentration determination and β-galactosidase liquid assay. Typically, 30 µl of extract were combined with 3 µl Mg 100× buffer ($MgCl_2$ 100 mM, β-mercaptoethanol 35%), 33 µl ONPG 8 mg/ml and 234 µl sodium phosphate 0.1M pH7.5. After incubation at 37° C., the reaction was stopped with 500 µl of 1M $Na_2CO_3$ and OD was measured at 415 nm. The relative β-galactosidase activity is determined as a function of this OD, normalized by the reaction time, and the total protein quantity.

2) Results

DmoCre is a chimeric protein including the $NH_2$-terminal moiety of I-DmoI fused to an I-CreI domain which cleaves hybrid DNA target with an half I-CreI cleavage site and a half I-DmoI site (C1D2, C2D2, FIG. 1). DmoCre is essentially active at 65° C., with little or no activity at 37° C. (Epinat, Arnould et al. 2003, Nucleic Acids Res 31: 2952-62). Dmo-Cre mutants with a putative enhanced activity at 37° C. were generated and assayed in yeast with procedures similar to those described in example 1, except that five different reporter plasmids were used: the plasmid bearing CUT8 (FIG. 3), and four similar plasmids that contain a single cleavage site, this site being either an I-CreI site, either an I-DmoI site, either C1D2, either C2D2 (FIG. 1). In addition, the DmoCre mutants were also tested in mammalian cells using a mammalian version of both the expression and the reporter plasmid.

The DmoCre mutants are summarized in Table II.

TABLE II

DmoCre mutants and cleavage activity in yeast and mammalian cells at 37° C.

| mutant | Cleavage profile in yeast | | | | Cleavage profile in CHO cells | | | |
|---|---|---|---|---|---|---|---|---|
| | I-CreI | I-DmoI | C1D2 | C2D2 | I-CreI | I-DmoI | C1D2 | C2D2 |
| DmoCre | − | − | − | − | − | − | − | − |
| A1V G20S | − | − | + | + | − | − | + | + |
| A1D G20S E45V N46T I69V | − | − | + | + | − | − | + | − |
| A1V G20S K30N L55P | − | − | + | + | − | − | + | + |
| A1V G20S L59Q | − | − | + | + | − | − | + | + |
| G20S N46D | − | − | + | + | − | − | + | − |
| G20S N46Y | − | − | + | + | − | − | + | + |
| A1V G20S N64K | − | − | + | + | − | − | + | + |
| I19N G20A L107R | − | − | + | + | − | − | + | + |
| A1V I19N G20S | − | − | + | + | − | − | + | + |
| I19N G20S F58S A108V | + | − | + | + | − | − | + | + |
| I19N G20S N46S L47Q N64T | − | − | + | + | − | − | + | + |
| A1V I19S G20A R104L | − | − | + | + | − | − | + | + |
| A1V I19T G20S | − | − | + | + | − | − | + | + |
| A1V I19T G20S N46I N64S | − | − | + | + | − | − | + | + |
| A1V I40T Q42L L55R | ND | − | − | − | ND | ND | ND | ND |
| A1V L15M I19T G20S | − | − | + | + | − | − | + | + |
| A1V L15Q G20S | + | − | + | + | − | − | + | + |
| A1V L15Q I19D G20S | + | − | + | + | + | − | + | + |
| L15R I19N G20S S44T | − | − | + | + | − | − | + | + |
| A1I M94K N102I | − | − | − | + | − | − | − | + |
| A1V N3D I10F I18V G20S N64D K66Q | − | − | + | + | − | − | + | + |
| A1V N3I G20S V38A | − | − | + | + | − | − | − | − |
| A1V N4I F109I | − | − | + | + | − | − | − | + |
| A1V N4Y G20S H51N | − | − | + | + | − | − | + | − |
| N6D G20S | − | − | + | + | − | − | + | + |
| S34C I52F G74V | ND | − | − | − | ND | ND | ND | ND |
| S8P I19T G20S N46D | − | − | + | + | − | − | + | + |
| A1V S8T G20S K26Q | − | − | + | + | − | − | + | + |
| A1V V7D I19L G20S T186A | − | − | + | + | − | − | + | + |
| A1V V7G G20S H51R L55R | + | − | + | + | − | − | − | + |
| A1V Y25F N32S V39A M56T Q70R | ND | − | − | − | ND | ND | ND | ND |

*Numeration of the amino acids is according to I-DmoI sequence SWISSPROT P21501 or structure PDB code 1b24. G20S mutation means amino acid 20 is G in DmoCre and S in the mutant.

One example of DmoCre mutant protein sequence (SEQ ID NO: 9) is displayed on FIG. 9. The majority of the mutants contain the G20S mutation, which by itself results in the strongest activity, as demonstrated with the dark blue staining obtained with the G20S mutant (FIG. 10). A similar cleavage profile could be observed in yeast and CHO cells, with the majority of the mutants being able to cut the C1D2 and C2D2 target. However, a few out of them did also cut an I-CreI DNA target, which suggest that these specific mutants could have a relaxed activity.

FIG. 10 also features mutants obtained by directed mutagenesis, such as I52F, L95Q. Such mutations were observed to result in an enhanced activity in I-DmoI at 37° C. Since DmoCre contains the NH2-terminal moiety of I-DmoI (up to amino acid 109) it could be expected that a I52F, L95Q (for example) version of DmoCre would also have an enhanced activity at 37° C. This was actually not observed, and none of these mutants had any effect on the activity of DmoCre at 37° C. Those results show that proposing mutations that could improve the activity of an enzyme based on results obtained on another molecule is not trivial even if the two proteins have a lot of common features.

The invention claimed is:

1. A polypeptide comprising residues 1-95, and optionally residues 96-109, of the sequence of SEQ ID NO: 2 or SEQ ID NO: 3, except that said polypeptide contains a substitution of at least: (i) one of the residues in positions 4, 20, 49, 52, 92, 94 and/or 95 of SEQ ID NO: 2 or SEQ ID NO: 3, and/or (ii) one of the residues in positions 101, 102, and/or 109 of SEQ ID NO: 2 or SEQ ID NO: 3, if present;
wherein said polypeptide shows increased cleavage activity at 37° C. against a DNA target it recognizes and cleaves in comparison to the cleavage activity of an identical polypeptide which does not comprise the substitutions of the residues specified in (i) and (ii) above against said DNA target.

2. The polypeptide according to claim 1, wherein the asparagine in position 4 is changed to isoleucine (N4I); the glycine in position 20 is changed to serine or alanine (G20S or G20A); the lysine in position 49 is changed to arginine (K49R); the isoleucine in position 52 is changed to phenylalanine (I52F); the alanine in position 92 is changed to threonine (A92T); the methionine in position 94 is changed to lysine (M94K); the leucine in position 95 is changed to glutamine (L95Q); the phenylalanine in position 101 (if present) is changed to cysteine (F101C); the asparagine in position 102 (if present) is changed to isoleucine (N 102I), and/or the phenylalanine in position 109 (if present) is changed to isoleucine (F109I).

3. The polypeptide according to claim 1 that is a mutant of I-DmoI comprising the substitution of at least one of the residues in positions 49, 52, 92, 95 and/or 101.

4. The polypeptide according to claim 3 that comprises at least the substitution of the isoleucine in position 52, and one or two additional substitutions of the residues in positions 49, 92, 95 and/or 101.

5. The polypeptide according to claim 4 that comprises substitutions selected from the group consisting of: a) K49R, I52F and L95Q, b) I52F and L95Q or c) I52F, A92T and F101C.

6. The polypeptide according to claim 3 that derives from the sequence SEQ ID NO: 1, 2 or 3.

7. The polypeptide according to claim 1 that is a mutant of a chimeric-Dmo endonuclease consisting of the fusion of the first I-Dmo I domain to a sequence of a dimeric LAGLIDADG (SEQ ID NO: 14) homing endonuclease or to a domain of another monomeric LAGLIDADG (SEQ ID NO: 14) homing endonuclease, said mutant comprising the substitution of at least: (i) one of the residues in positions 4 or 20 and/or 94, and/or (ii) one of the residues in positions 102 or 109, if present.

8. The polypeptide according to claim 7, wherein the first I-DmoI domain is at the NH$_2$-terminus of said chimeric-Dmo endonuclease.

9. The polypeptide according to claim 7 that comprises a linker, preferably an I-DmoI linker consisting of at least 6 consecutive residues from the fragment 96 to 104 of I-DmoI.

10. The polypeptide according to claim 7 that comprises substitutions selected from the group consisting of: a) G20S, b) G20A, c) M94K and N 102I, or d) N4I and F109I.

11. The polypeptide according to claim 7, wherein said dimeric LAGLIDADG (SEQ ID NO: 14) homing endonuclease is I-CreI.

12. The polypeptide according to claim 11, that derives from the sequence of any one of SEQ ID NOS: 5 to 8.

13. A heterodimeric-Dmo endonuclease, comprising the polypeptide according to claim 1, and a second polypeptide comprising a sequence of a dimeric LAGLIDADG (SEQ ID NO: 14) homing endonuclease or a domain of another monomeric LAGLIDADG (SEQ ID NO: 14) homing endonuclease.

14. The heterodimeric Dmo-endonuclease according to claim 13, wherein said dimeric LAGLIDADG (SEQ ID NO: 14) homing endonuclease is I-CreI.

15. The polypeptide according to claim 1, further comprising a tag at its NH$_2$ and/or COOH terminus.

16. A polynucleotide encoding the polypeptide according to claim 1.

17. A vector comprising the polynucleotide according to claim 16.

18. A host cell modified by the polynucleotide according to claim 16.

19. The polypeptide of claim 4 that comprises a substitution of the isoleucine residue at position 52 to phenylalanine (I52F).

20. A polypeptide comprising the first domain of I-DmoI, except that said polypeptide contains a substitution of at least: (i) one of the residues that directly align with those in positions 4, 20, 49, 52, 92, 94 and/or 95 of SEQ ID NO: 2 or SEQ ID NO: 3, and/or (ii) one of the residues that directly align with those in positions 101, 102, and/or 109 of SEQ ID NO: 2 or SEQ ID NO: 3, if present;
wherein said polypeptide shows increased cleavage activity at 37° C. against a DNA target it recognizes and cleaves in comparison to the cleavage activity of an identical polypeptide which does not comprise the substitutions of the residues specified in (i) and (ii) above against said DNA target.

21. An endonuclease comprising the polypeptide of claim 1 and (i) a second I-Dmo domain, (ii) a sequence of a dimeric LAGLIDADG homing endonuclease, or (iii) a domain of a monomeric LAGLIDADG homing endonuclease.

22. An endonuclease comprising the polypeptide of claim 20 and (i) a second I-Dmo domain, (ii) a sequence of a dimeric LAGLIDADG homing endonuclease, or (iii) a domain of a monomeric LAGLIDADG homing endonuclease.

* * * * *